US007901193B2

(12) United States Patent
Evans et al.

(10) Patent No.: US 7,901,193 B2
(45) Date of Patent: Mar. 8, 2011

(54) PUMP ASSEMBLY FOR THERAPEUTIC INFLATABLE CELL APPARATUS

(76) Inventors: John James Henry Evans, Barton-on-Sea (GB); Christopher Peter Evans, Lymington (GB)

( * ) Notice: Subject to any disclaimer, the term of this patent is extended or adjusted under 35 U.S.C. 154(b) by 931 days.

(21) Appl. No.: 11/325,803

(22) Filed: Jan. 5, 2006

(65) Prior Publication Data

US 2006/0184079 A1 Aug. 17, 2006

(30) Foreign Application Priority Data

Jan. 6, 2005 (GB) .................................. 0500117.7

(51) Int. Cl.

| | |
|---|---|
| ***F04B 39/10*** | (2006.01) |
| ***A61M 29/00*** | (2006.01) |
| ***A47C 27/08*** | (2006.01) |
| ***A61H 7/00*** | (2006.01) |

(52) U.S. Cl. ......... 417/442; 606/192; 601/149; 601/150; 5/713; 5/715

(58) Field of Classification Search .................. 417/442; 600/16–18, 20, 21, 31, 39; 606/192, 202, 606/203; 601/149, 150

See application file for complete search history.

(56) References Cited

U.S. PATENT DOCUMENTS

| | | | | |
|---|---|---|---|---|
| 4,619,481 | A * | 10/1986 | Grudzinskas | 297/284.1 |
| 5,117,518 | A * | 6/1992 | Schild | 5/713 |
| 5,144,956 | A * | 9/1992 | Souma | 600/495 |
| 5,233,974 | A * | 8/1993 | Senoue et al. | 601/149 |
| 5,464,019 | A * | 11/1995 | Anderson et al. | 600/490 |
| 5,611,772 | A * | 3/1997 | Fujimoto et al. | 601/149 |
| 6,058,538 | A * | 5/2000 | Chapman et al. | 5/713 |
| 6,216,300 | B1 * | 4/2001 | Hannagan | 5/713 |
| 6,224,538 | B1 | 5/2001 | Wang et al. | |
| 6,412,129 | B1 | 7/2002 | Wu | |
| 6,877,178 | B2 * | 4/2005 | Chapman et al. | 5/713 |
| 2002/0115949 | A1 | 8/2002 | Kuslich et al. | |
| 2004/0068214 | A1 | 4/2004 | Evans et al. | |

FOREIGN PATENT DOCUMENTS

| | | | |
|---|---|---|---|
| EP | 0 880 959 | A2 | 12/1998 |
| GB | 2064330 | A | 6/1981 |
| GB | 2389798 | A | 12/2003 |
| WO | WO 02/15835 | A1 | 2/2002 |

* cited by examiner

*Primary Examiner* — Charles G Freay
(74) *Attorney, Agent, or Firm* — Wegman, Hessler & Vanderburg

(57) ABSTRACT

A pump assembly (200) for therapeutic inflatable cell apparatus, the assembly comprising a common pump unit (210), control means (160), and, first and second valve means (201; 202), each valve means comprising a cycle control valve means, said cycle control valve means being provided with at least one fluid passageway and each valve means being adapted to be positioned to predetermined conditions so as to regulate fluid quantity in respective therapeutic inflatable cell apparatus, each valve means is adapted to perform at least one respective inflation/deflation sequence, and the assembly being such that, in use, on air being required by a valve means at a particular instance during the respective inflation/deflation sequence, the control means activates the common pump unit and air is pumped to an air outlet to feed air to the at least two valve means, and the pump assembly being such that the first and second valve means are operable both singularly and simultaneously.

14 Claims, 20 Drawing Sheets

PUMP ASSEMBLY FOR THERAPEUTIC INFLATABLE CELL APPARATUS

CROSS-REFERENCE TO RELATED APPLICATION

This application claims the priority filing benefit of Great Britain Application No. GB 0500117.7 filed Jan. 6, 2005.

BACKGROUND OF THE INVENTION

1. Field of Invention

The present invention relates to pump assemblies, and in particular to pump assemblies for therapeutic inflatable cell apparatus.

2. Description of Related Art

Therapeutic inflatable cell apparatus are generally of two types, pressure relieving supports and compression therapy garments. Pressure therapy garments are adapted to be secured around a specific limb (for example a calf, a thigh or a foot) of a patient. Control of such garments is conventionally effected by a pneumatic pump unit.

Pressure relieving supports are typically in the form of mattresses and cushions and comprise multiple inflatable cells which are sequentially inflated and deflated to provide appropriate pressure area therapy.

SUMMARY OF THE INVENTION

The present invention seeks to provide an improved pump assembly for therapeutic cell apparatus.

According to the invention there is provided a pump assembly for therapeutic inflatable cell apparatus, the assembly comprising a common pump unit, control means, and, first and second valve means, each valve means comprising a cycle control valve means, said cycle control valve means being provided with at least one fluid passageway and each valve means being adapted to be positioned to predetermined conditions so as to regulate fluid quantity in respective therapeutic inflatable cell apparatus, each valve means is adapted to perform at least one respective inflation/deflation sequence, and the assembly being such that, in use, on air being required by a valve means at a particular point during the respective inflation/deflation sequence, the control means activates the common pump unit and air is pumped to an air outlet to feed air to the at least two valve means, and the pump assembly being such that the first and second valve means are operable both singularly and simultaneously.

In a highly preferred embodiment the inventive assembly advantageously allows multiple inflatable cell apparatus to operate simultaneously and at least two of the inflatable cell apparatus being subjected to different inflation/deflation sequences. For example, an inflatable support and two pressure garments could be operated simultaneously from the inventive pump assembly. In one embodiment more than two different types of inflatable cell apparatus are capable of being inflated/deflated by the pump assembly.

An inflation/deflation sequence preferably comprises at least one or a combination of (i) inflating at least one cell of an inflatable cell apparatus to a particular pressure, (ii) maintaining a predetermined pressure in at least one cell of an inflatable cell apparatus for a predetermined time, (iii) inflating and/or deflating cells in a predetermined sequence, (iv) inflating and/or deflating at least one cell at a particular rate of inflation and/or deflation.

The common pump unit preferably consists of one pneumatic pump unit.

Preferably the cycle control means comprises a rotatable valve member which is adapted to be rotated to predetermined angular positions.

Preferably where the inflatable cell apparatus comprises a plurality of cells the predetermined conditions are indexed so that the cells can be selectively inflated.

Preferably each valve means further comprises a static valve member, said static valve member being provided with at least one fluid passageway which is adapted to be communicable with the inflatable cell apparatus and the rotatable valve member being arranged to be rotatable with respect to the static valve member. Most preferably the inflatable valve member is adapted to be rotated into a position in which said at least one fluid passageway of the rotatable valve member is in fluid communication with the at least one fluid passageway of the static valve member.

The rotatable valve member is desirably provided with at least one fluid passageway for inflation of at least part of the inflatable cell apparatus and with at least one fluid passageway for deflation of at least part of the inflatable cell apparatus, and in use the rotatable valve member can be rotated to predetermined angular positions to effect at least one of inflation and deflation of the apparatus.

Most preferably two passageways for inflation are provided which are angularly spaced by 180°.

In a highly preferred embodiment the rotatable valve member is rotatable with respect to the static valve member so as to determine whether a fluid passageway of the static valve member is brought into fluid communication with either an inflation passageway or a deflation passageway of the rotatable valve member.

Preferably the static valve member comprises a plurality of fluid passageways, each fluid passageway being associated with a respective cell of an inflatable cell apparatus.

In a preferred embodiment the static valve member is provided with at least two sets of a plurality of fluid passageways, each set of passageways being adapted to be associated with a respective inflatable cell apparatus.

In preferred embodiments, said fluid passageways of the rotatable valve member and the static valve member extend from one side of the respective valve member to an opposite side of the respective valve member.

Channels are desirably formed in an outer surface in the static valve member, the channels being in fluid communication with fluid passageways of the static valve member, and said channels extending substantially laterally of the fluid passageways.

At least two fluid passageways may be fluidically connected by a channel.

The control means is preferably provided with control data, the control data being representative of instructions for controlling the pump unit and the valve means to perform at least one inflation/deflation sequence. Most preferably at least one set of instructions is stored for respective inflation/deflation sequences for each of the first and second valve means.

The control means is most preferably linked to a position sensor for sensing the angular position of the valve means and to a pressure sensor for measuring pressure in at least one cell of an inflatable cell apparatus. The control means is preferably configured to control the pump means and the valve means in response received signals from the position sensor and the pressure sensor, compare said pressure and position signals to the control data and operate the valve means and/or the pump means as required.

The control means is preferably configured to adjust the angular position of the rotatable valve member to a desired angular position in response to a first signal relating to a current angular position, and in response to a second signal relating to angular displacement of the rotatable valve member during movement thereof to the desired angular position, said second signal being issued by the position sensor.

The control means preferably comprises a rotatable component which is connected to the rotatable valve member and is provided with a plurality of angularly spaced index features, and the control means further comprising a radiation sensor, and in use, rotation of the rotatable component causes the index features to selectively control radiation received by the sensor.

At least one valve means is provided with an associated socket which is adapted to receive a plug of therapeutic inflatable cell apparatus.

Conveniently where the control means comprises RAM (Random Access Memory) a user may input a desired set of inflating/deflating control instructions to be stored by the data storage device.

BRIEF DESCRIPTION OF THE DRAWINGS

Various embodiments of the invention will now be described, by way of example only, with reference to the accompanying drawings in which.

DETAILED DESCRIPTION OF THE PREFERRED EMBODIMENT

Figure 1:
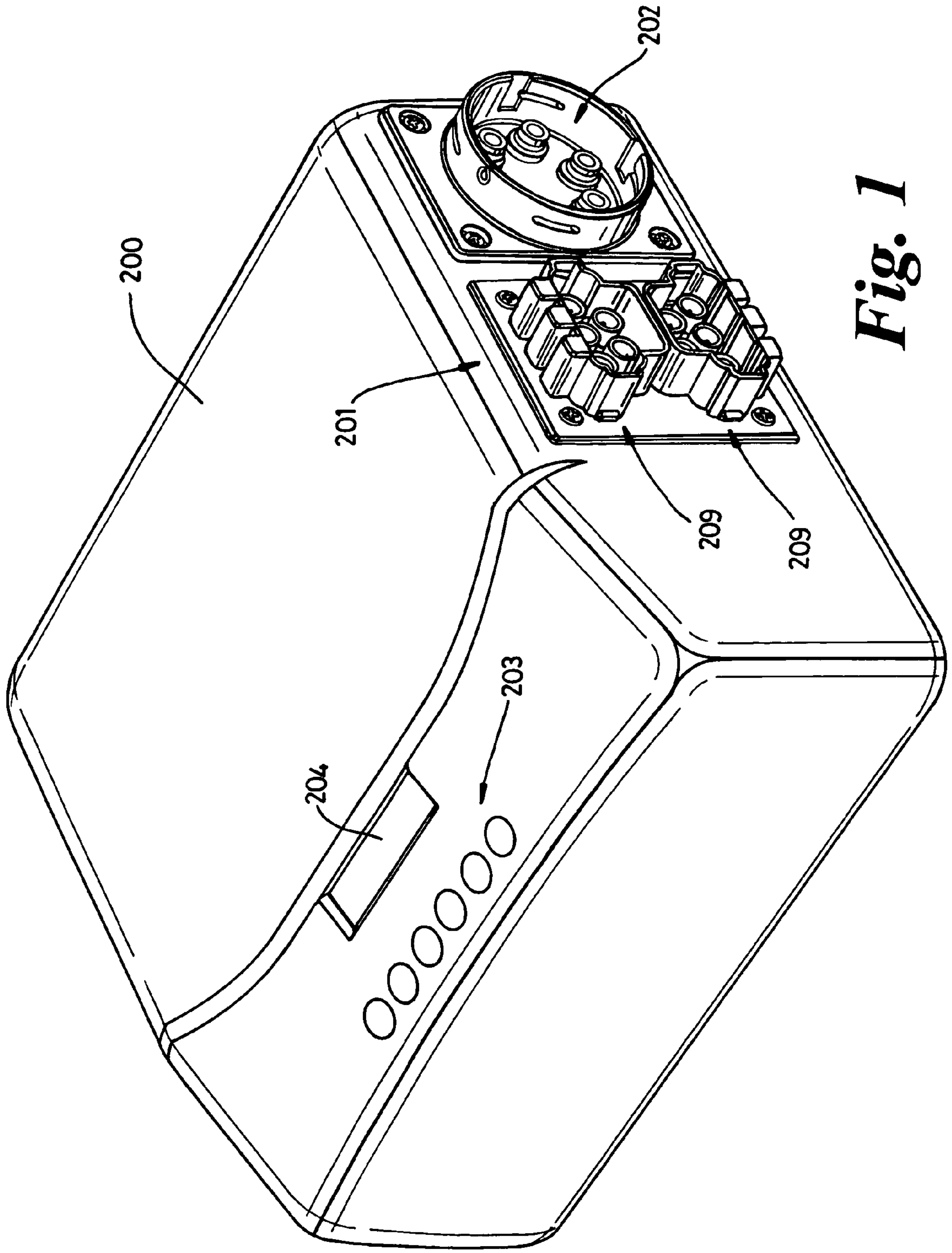
FIG. 1 shows a perspective view of a pump assembly for therapeutic inflatable cell apparatus.

FIG. 1 shows a portable pneumatic pump assembly 200 for therapeutic inflatable cell apparatus, the assembly being provided with a first valve/socket assembly 201 and a second valve/socket assembly 202, the first valve socket assembly comprising a pair of sockets 209. Each valve/socket assembly comprising a rotatable valve member which regulates air to and from an inflatable cell apparatus attached to each valve/socket assembly, with air being provided by a common pneumatic pump unit 210. The pump assembly 200 is provided with a control panel comprising a keypad 203 for user input and a display screen 204.

Figure 4:
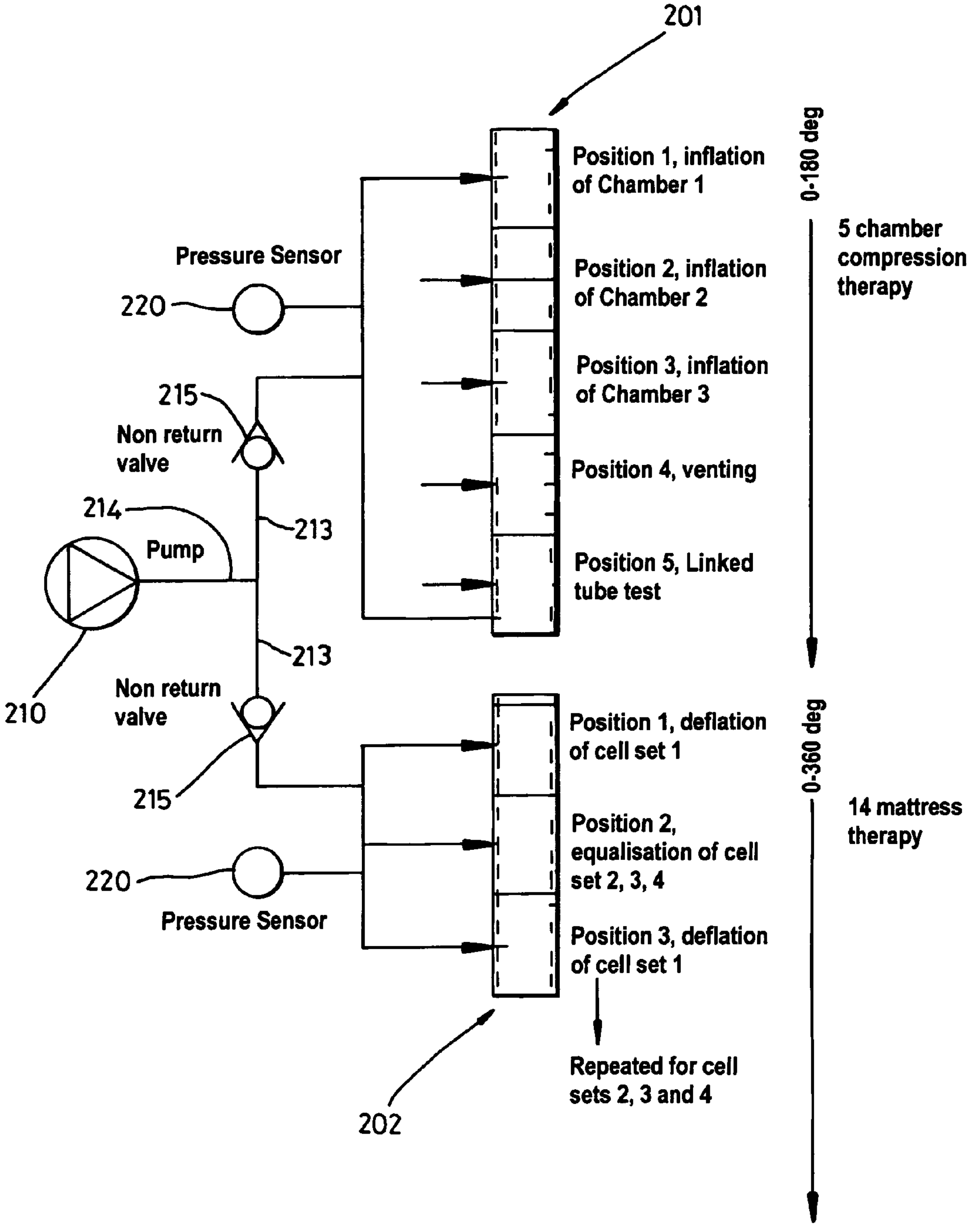
FIG. 4 is a schematic representation of the pump unit and the valve/socket arrangements of the assembly of FIG. 1.
Figure 5:
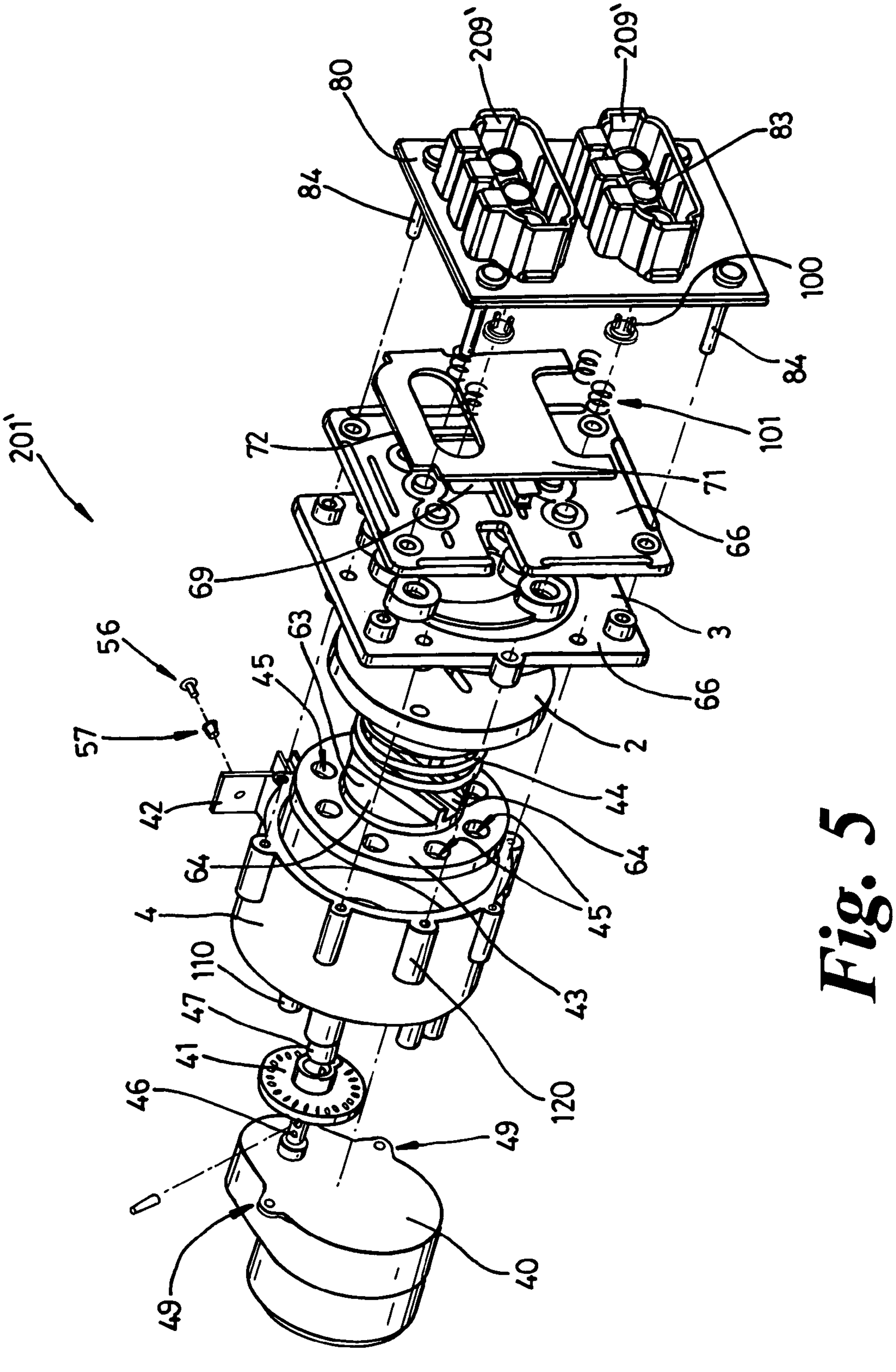
FIG. 5 is an exploded front isometric view of part of pneumatic pump assembly in accordance with the invention.

Each valve/socket arrangement comprises a rotatable valve member 2, a static valve member 3, the rotatable valve member 2 being arranged to be rotatable with respect to the static valve member 3. The valve components of a valve/socket arrangement 201' (which is very similar to arrangement 201) comprising two sockets 209', is now discussed, in which it is also to be noted that the valve components of the arrangement 202 are very similar to the arrangement 201' save for a different airway configuration (as best seen in FIG. 4) and a different socket.

Figure 10:
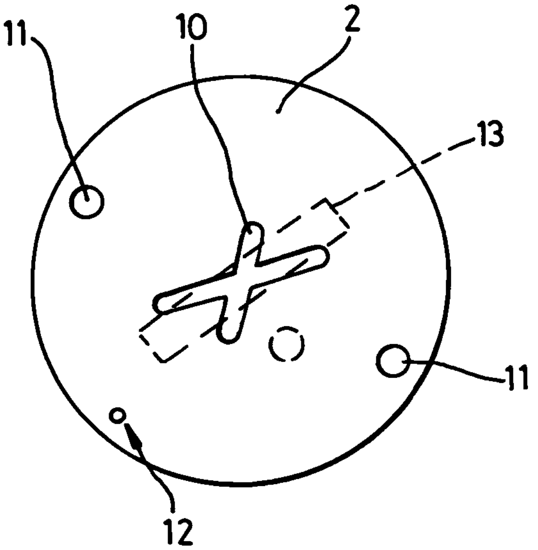
FIG. 10 is a front elevation of the rotatable valve member shown in FIGS. 1 and 2.
Figure 11:
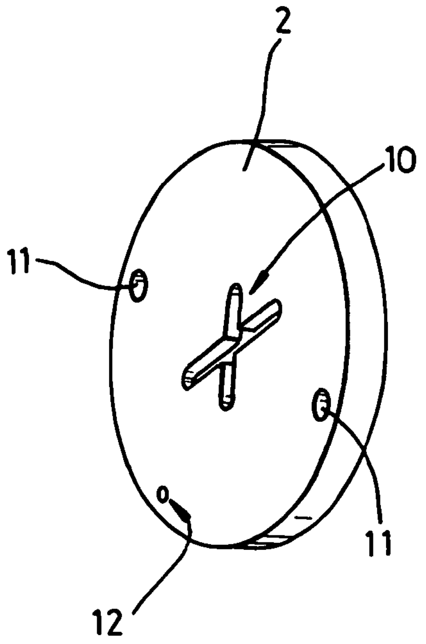
FIG. 11 is a front isometric view of the rotatable valve member shown in FIG. 6.
Figure 12:
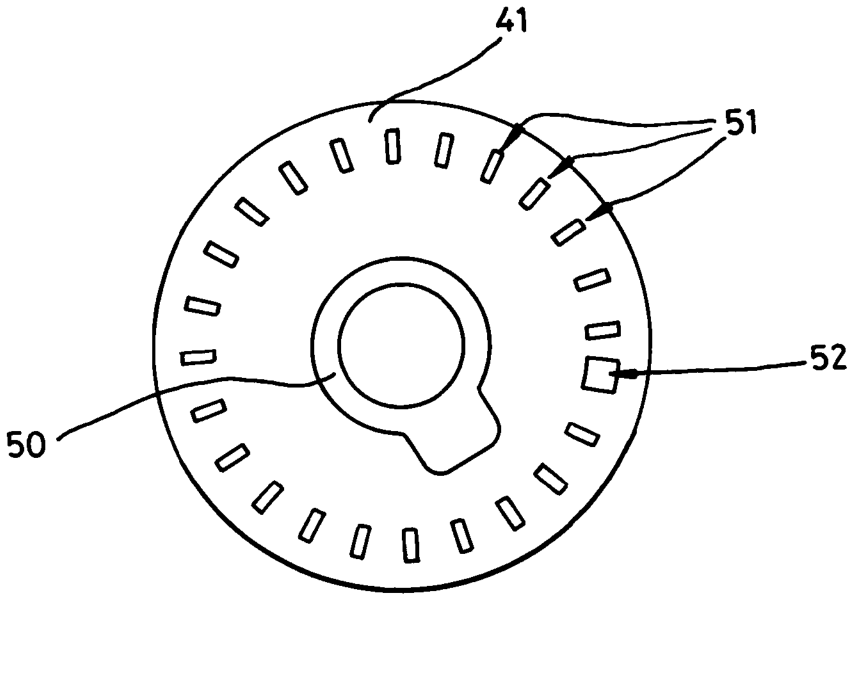
FIG. 12 is a front elevation of the optical disc shown in FIGS. 1 and 2.
Figure 13:
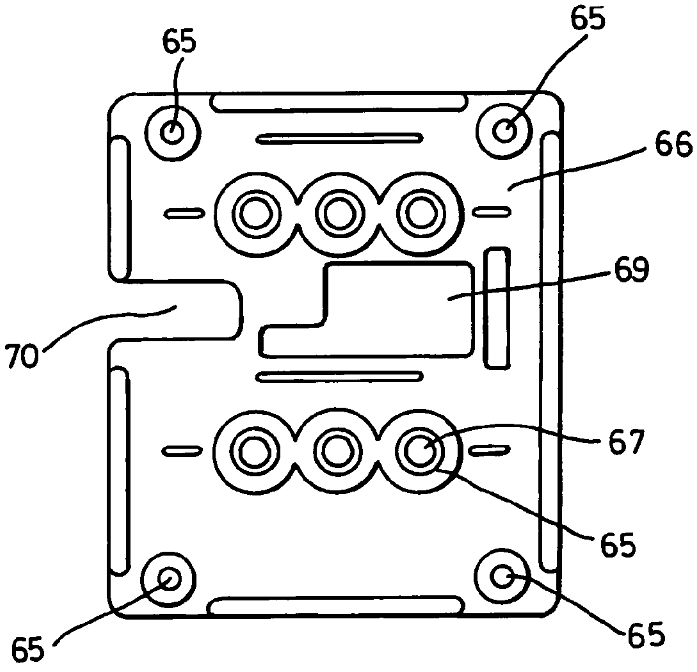
FIG. 13 is a front elevation of the intermediate plate shown in FIGS. 1 and 2.
Figure 14:
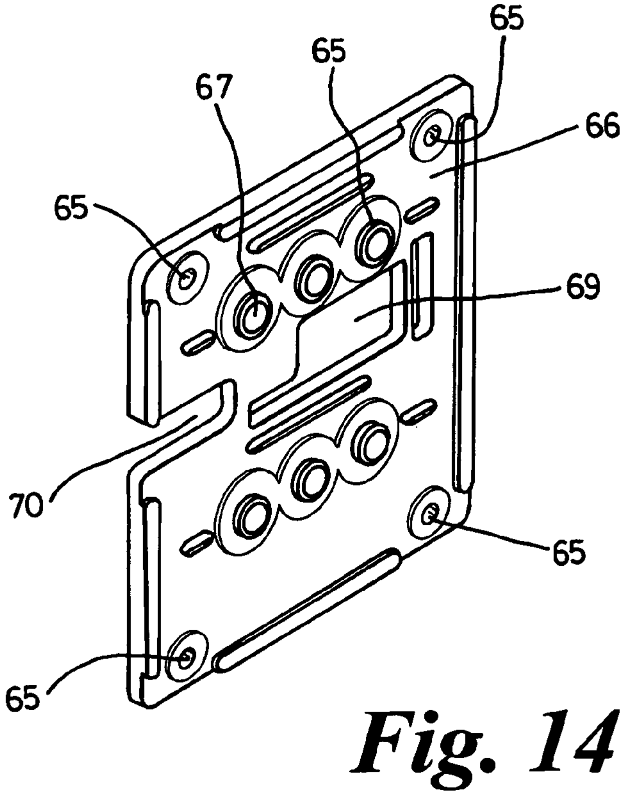
FIG. 14 is a front isometric view of the intermediate plate shown in FIG. 9.
Figure 15:
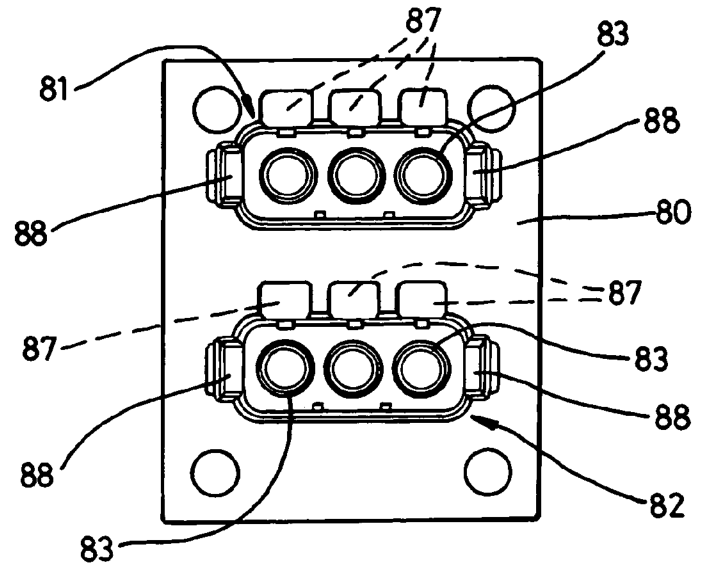
FIG. 15 is a front elevation of the connector plate shown in FIGS. 1 and 2.
Figure 16:
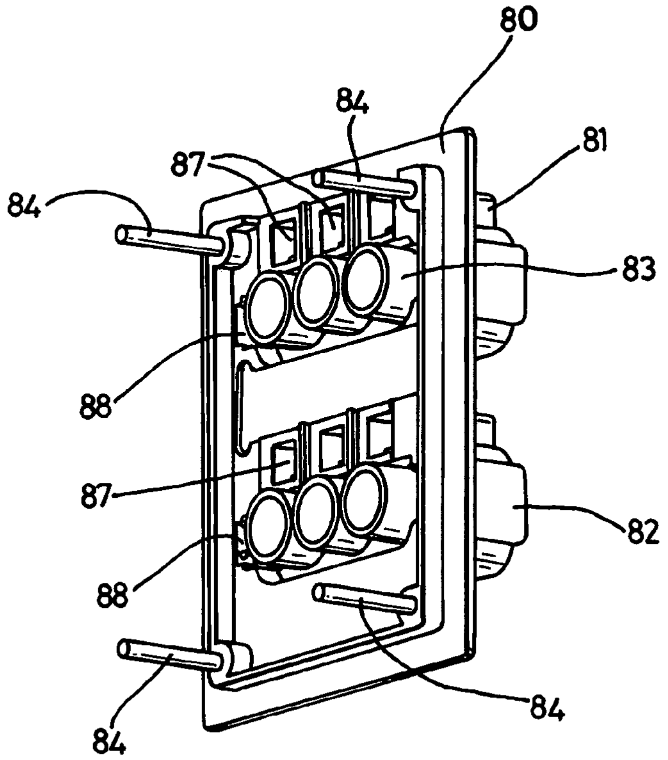
FIG. 16 is a rear isometric view of the connector plate shown in FIG. 11.

With further reference to FIGS. 10 and 11 the rotatable valve member 2 is of disc-like form and is provided with a ‘blind’ recess 10 of substantially skewed X-shape which is formed in the front surface thereof. The valve member 2 further comprises two through-holes 11 forming fluid passageways which are angularly spaced by 180° about the centre point of the valve member 2.

A third though-hole 12 is provided in the rotatable valve member 2 of which the angular separation from each of the holes 11 is 75° in each case.

The rearward surface of the rotatable valve member 2 is provided with rib 13 which extends in a direction which is substantially parallel to the diameter of the valve member.

Figure 7:
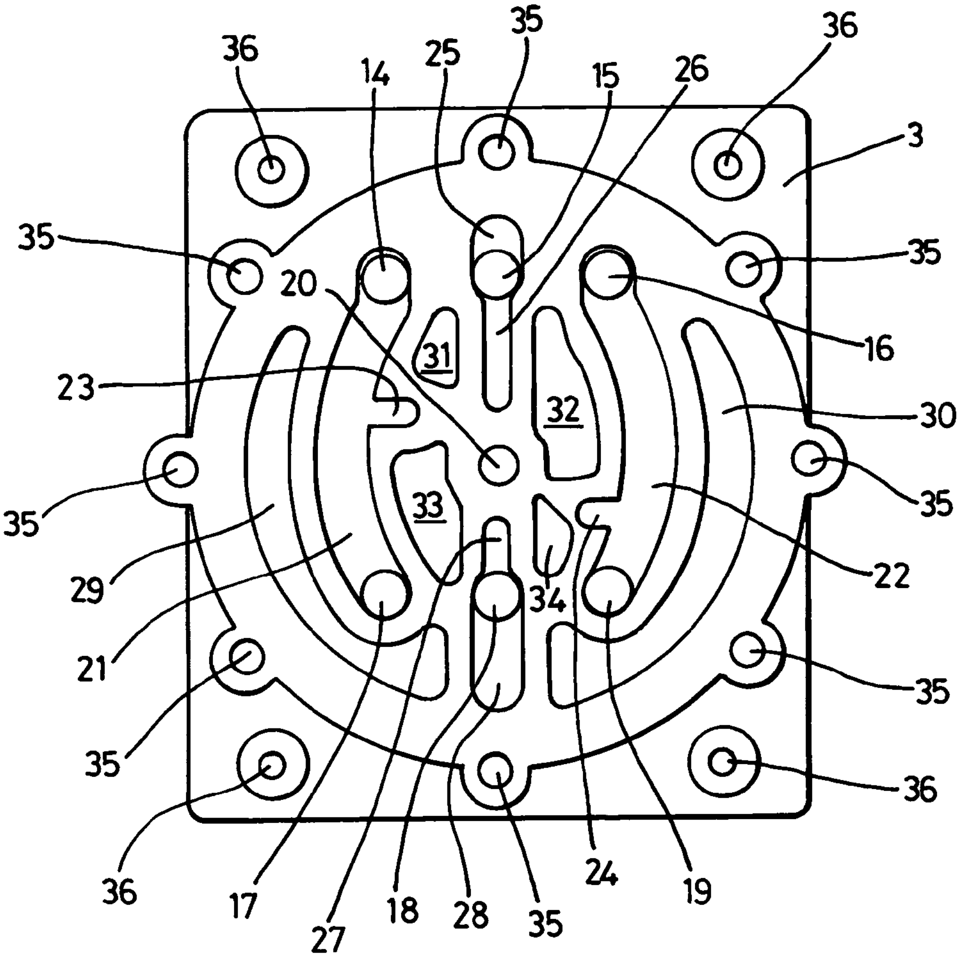
FIG. 7 is a rear elevation of the static valve member shown in FIGS. 1 and 2.
Figure 8:
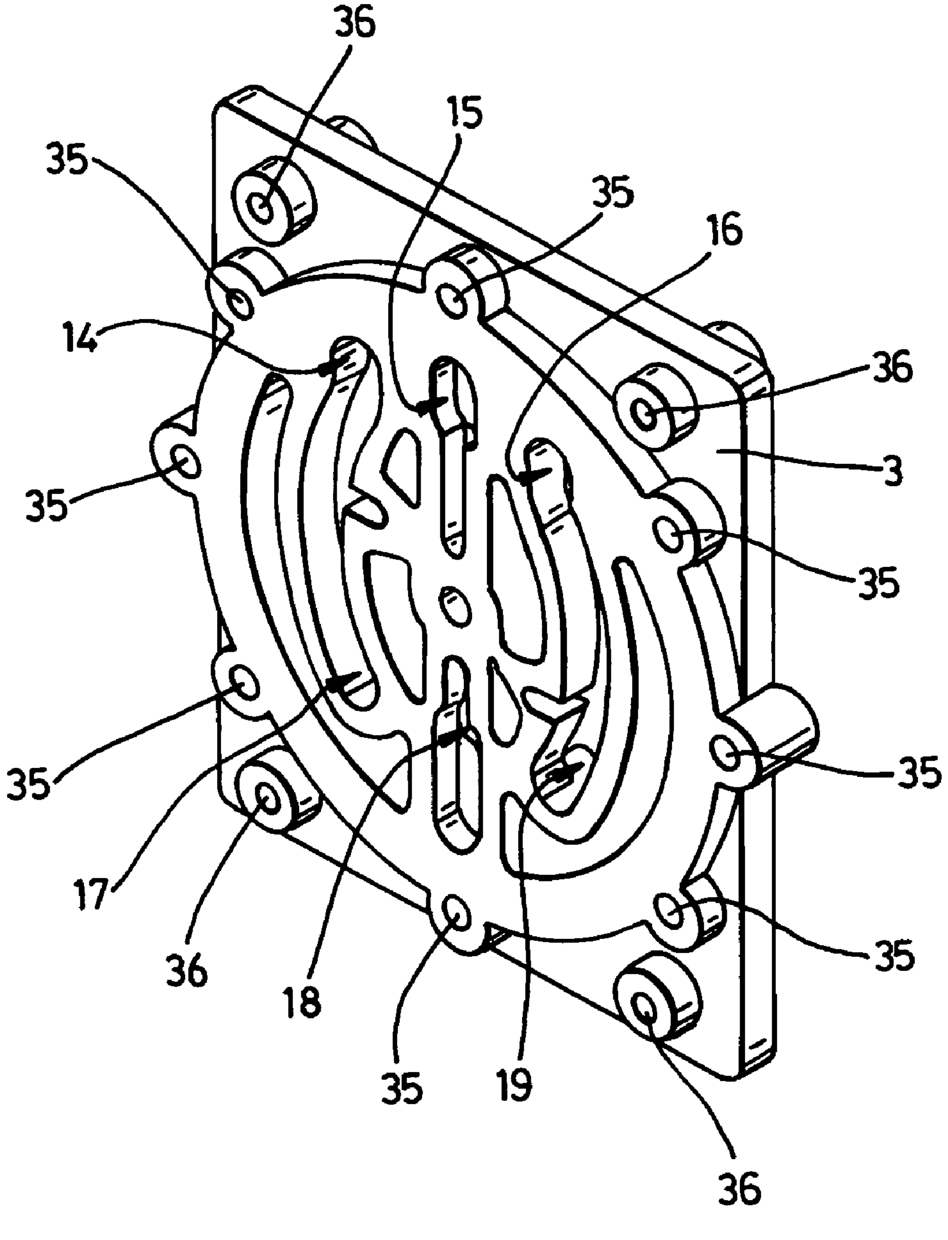
FIG. 8 is a rear isometric view of the static valve member shown in FIG. 3.
Figure 9:
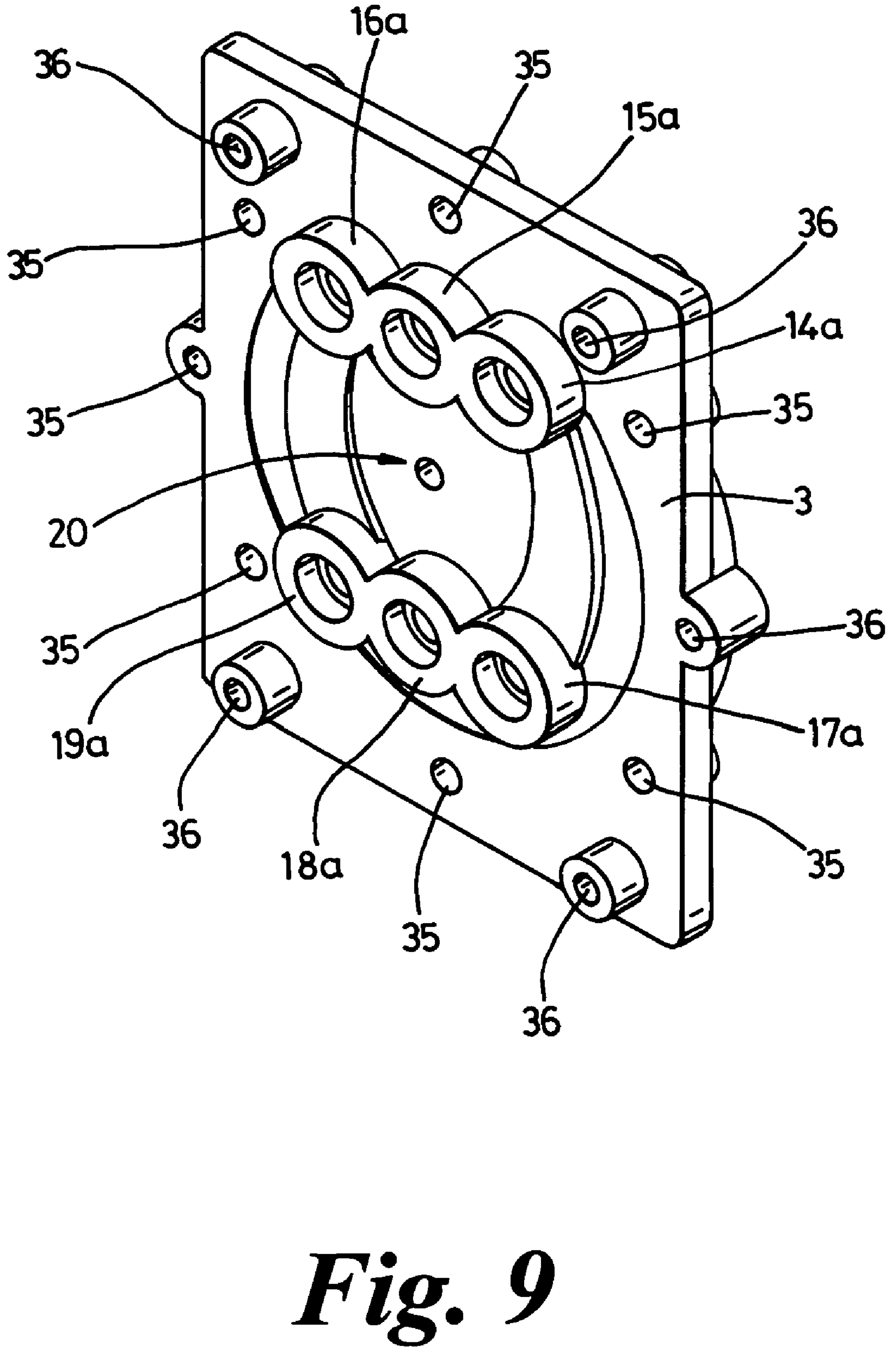
FIG. 9 is a front isometric view of the static valve member shown in FIGS. 3 and 4.

With reference in particular to FIGS. 7, 8 and 9 the static valve member 3 is essentially of plate like form and is provided with a first set of horizontally aligned ports 14, 15 and 16 and a second set of horizontally aligned ports 17, 18 and 19, said ports providing fluid passageways. A port 20 is also provided in the static valve member 3 which is located substantially centrally of said valve member.

As seen best in FIGS. 9 and 10 channels 21 and 22, which are of substantially arcuate outline, provide fluid communication between ports 14 and 17, and ports 16 and 19 respectively. The channels 21 and 22 are provided with branch channel positions 23 and 24 respectively which extend substantially horizontally towards the vertical axis of the static valve member 3.

The ports 15 and 18 which are located centrally of each set of ports are each provided with upper and lower channel portions which are in fluid communication with the respective port. The port 15 is provided with an upper channel portion 25 and a lower channel portion 26, and the port 18 being provided with upper channel portion 27 and lower channel portion 28.

The rearward face of the static valve member 3 is also provided with a plurality of pressure relief recesses 31, 32, 33 and 34.

Turning to FIG. 9 showing the front face of the static valve member 6 each port 14, 15, 16, 17, 18 and 19 there is an associated outwardly extending annular wall 14*a*, 15*a*, 16*a*, 17*a*, 18*a* and 19*a* respectively.

Equally angularly spaced around the ports 14, 15, 16, 17, 18, 19 and 20 and arranged in a circular formation, a first set of eight attachment through-holes 35 are provided. The static valve member 3 is also provided with a second set of four attachment through-holes 36 which are located towards the corners of the valve member 3.

The valve/socket assembly 201' further comprises a motor 40, an optical disc 41, a sensor 42, a transmission disc 43 and a spring 44.

The motor 40 comprises an output shaft portion 46 onto which is rotatably mounted the optical disc 41. The shaft portion 46 is received in a collar 47 and is fast with the optical disc 41. The collar 47 passes through the disc 41 and through two sleeves 50 which are provided on opposite sides of the disc 41. The shaft portion 46 extends through an aperture in cylindrical housing 48 and the distal end of said collar 47 is fixedly attached to the rearward face of the transmission disc 43.

The optical disc 41 is provided with twenty three slots 51 and one slot 52, the slots 51 and 52 are angularly spaced around the disc 41 and the slot 52 being slightly wider than the slots 52.

A position sensor device 42 is attached to bracket 55 by way of a two-piece fastener arrangement shown at 56 and 57. The sensor device may generally be described as a phototransistor device which comprises two limbs 60 and 61 which are spaced such that in use they flank the optical disc 41. The limb 60 is provided with an inwardly directed light emitting device (not shown) and the limb 61 is provided with a light sensor (not shown) which is directly opposite the light emitting device.

The transmission disc 43 is provided with eight equally angularly spaced ports 45 and comprises a locating formation 63 on the front face thereof. The locating formation 63 comprises two spaced walls 64 which are adapted to receive the rib 13 of the rotatable valve member 2.

The spring 44 is adapted to fit over the locating formation 63 and the rib 13 and so be interposed between the transmission disc 43 and the rotatable valve member 2.

Located adjacent to the front face of the static valve member 3 there is provided an intermediate plate 66. The intermediate plate 66 is provided with two sets of three ports 67 which are arranged to correspond with the arrangement of the ports 14, 15, 16, 17, 18 and 19 of the static valve member 3. Each port 67 comprises an outwardly extending conduit portion 68 on front and rear faces of the intermediate plate 66.

The intermediate plate 66 is provided with two cut-outs 69 and 70 which are located generally between the two sets of ports 67. The intermediate plate is further provided with four attachment holes 73 which are located towards each corner of the plate.

Moving further forward there is provided a plate 71. The plate 71 is provided with two cut-outs 72 and 73 which are dimensioned to accommodate the conduit ports 68 of the intermediate plate 66.

The connector plate 80 is formed with the two socket formations 209' which are each adapted to receive one of the garment plug of a garment or a support. Each socket formation 209' comprises three connection conduits 83 each of which, in use, corresponds to an associated inflatable cell or group of cells of a pressure therapy garment or pressure relief support.

Figure 6:
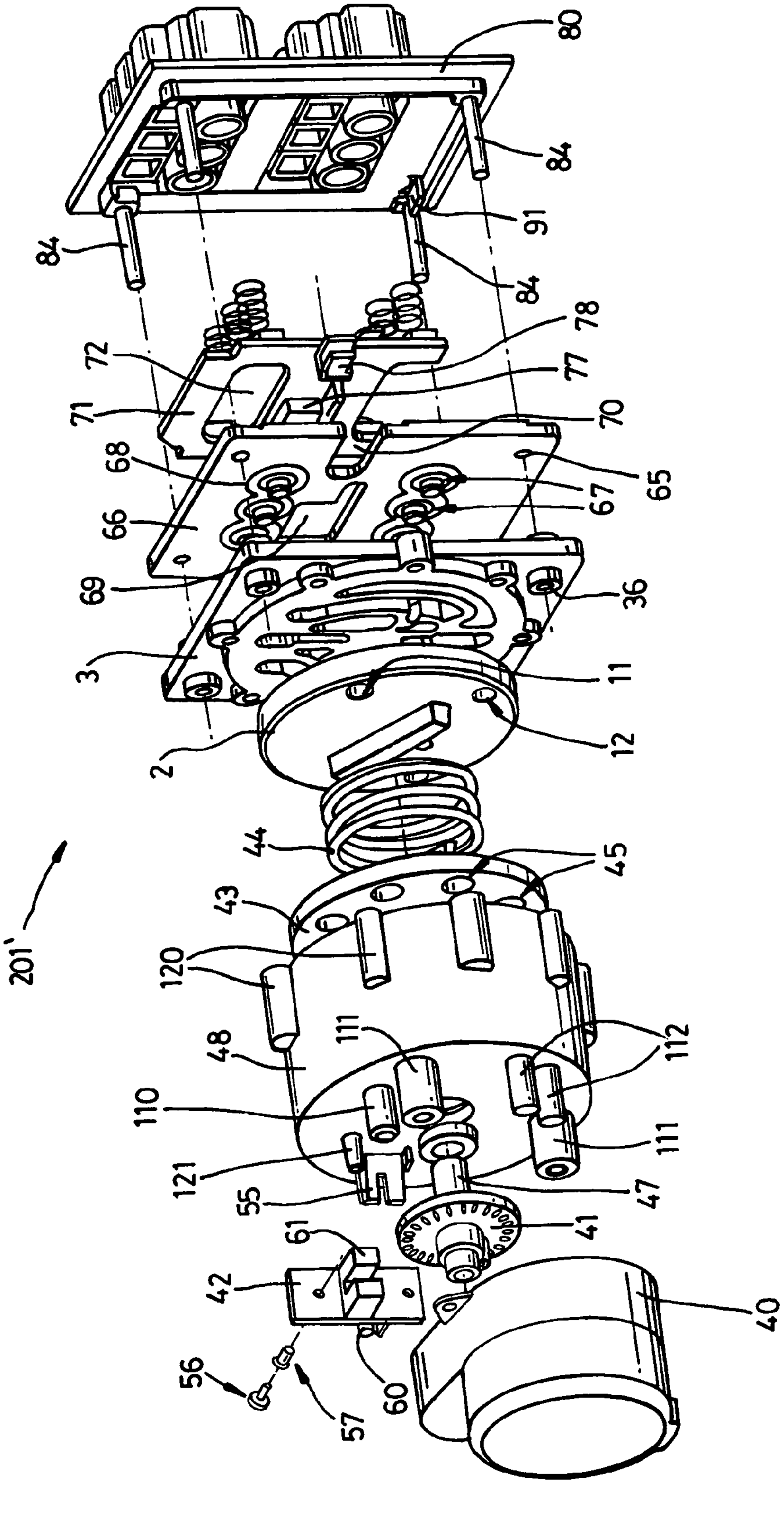
FIG. 6 is an exploded rear view of the part of the pneumatic pump assembly shown in FIG. 1.

The rearward ends of the conduits 83 are each provided with a non-return or shut-off valve arrangement which comprises a valve plate 100 and a spring 101. The valve plates 100 each comprise four guide limbs 105 which are configured to be received in a respective conduit 83. (Valve plates 100 are omitted from FIG. 6 for reasons of clarity.)

Figure 26:
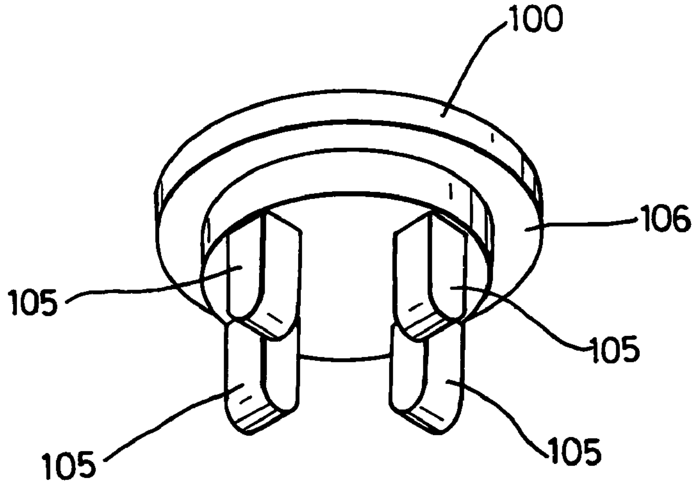
FIG. 26 is a perspective view of a non-return valve.
Figure 27:
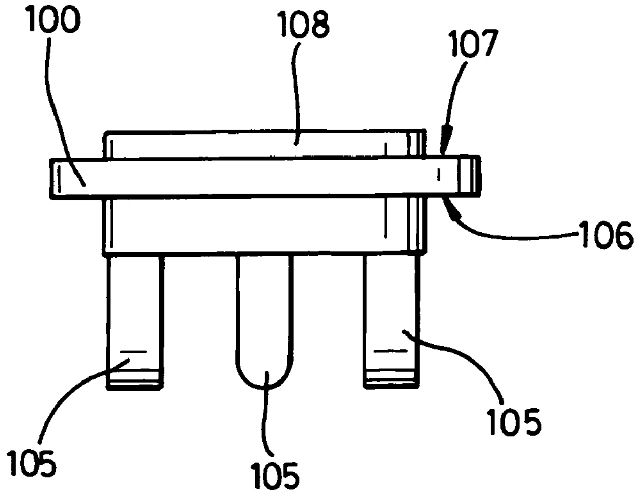
FIG. 27 is a side elevation of the non-return valve of FIG. 26.

A front facing annular shoulder 106 is provided around the guide limbs 105 and is axially spaced from the bases thereof. In use the shoulder 106 receives an o-ring seal (omitted from FIGS. 26 and 27).

The valve plate 100 is provided on the rear facing surface thereof with an annular shoulder 107 which is adapted to locate one end of the respective spring 101.

Figure 2:
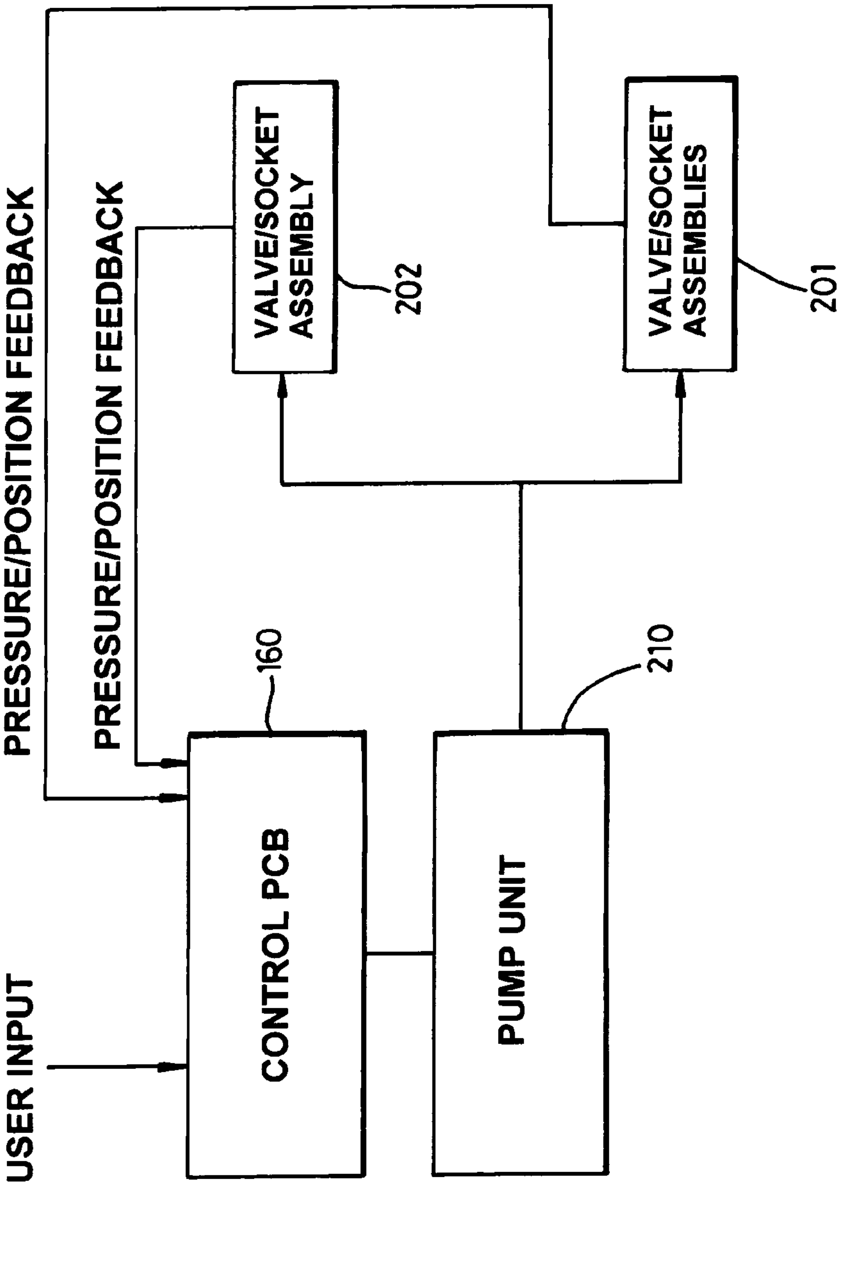
FIG. 2 is a block diagram of the various components of the assembly of FIG. 1.
Figure 22:
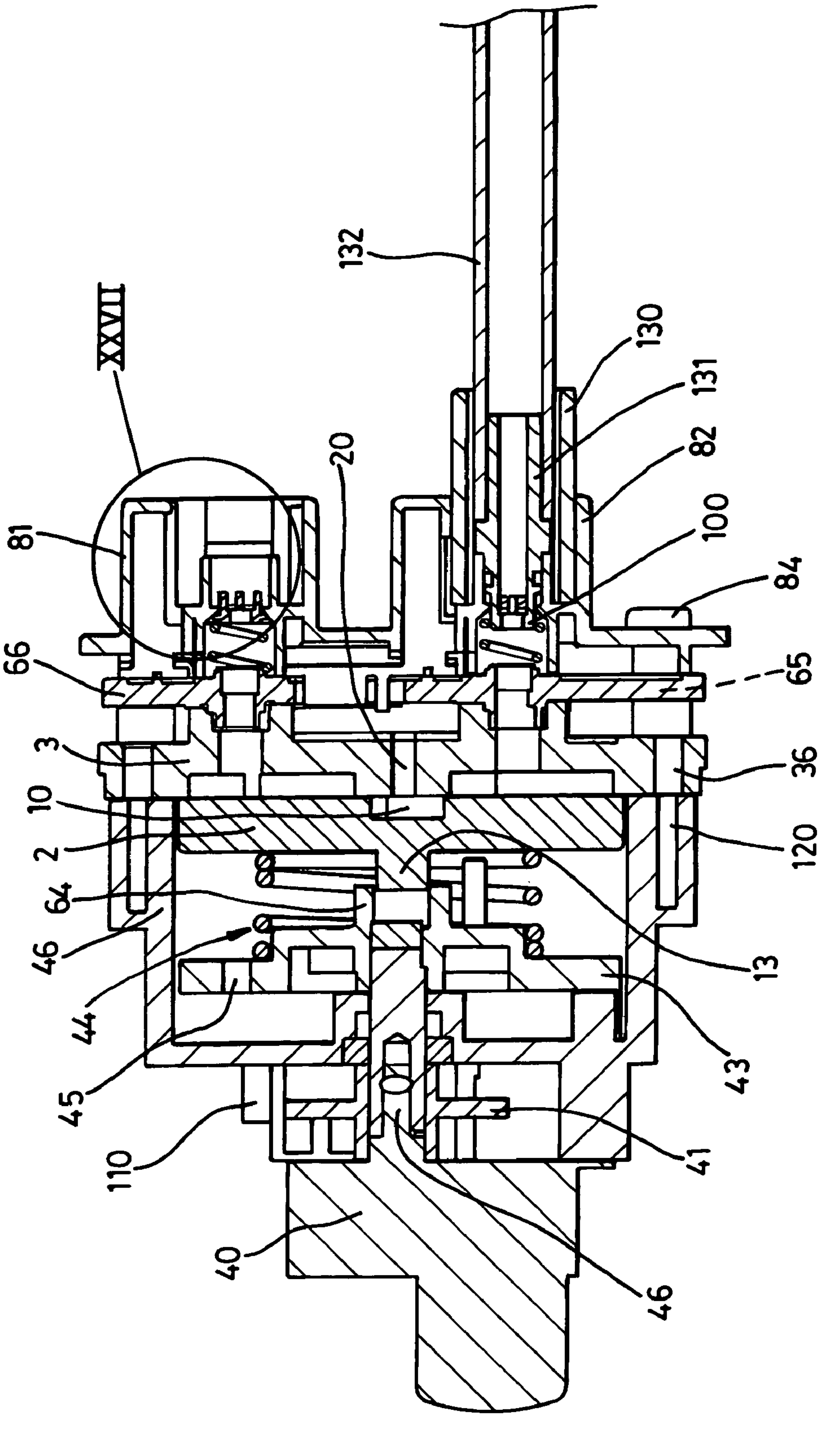
FIG. 22 is a (somewhat schematic) cross-section of the components shown in FIGS. 1 and 2 in an assembled state in which one plug has been inserted into one of the sockets of the connector plate.
Figure 23:
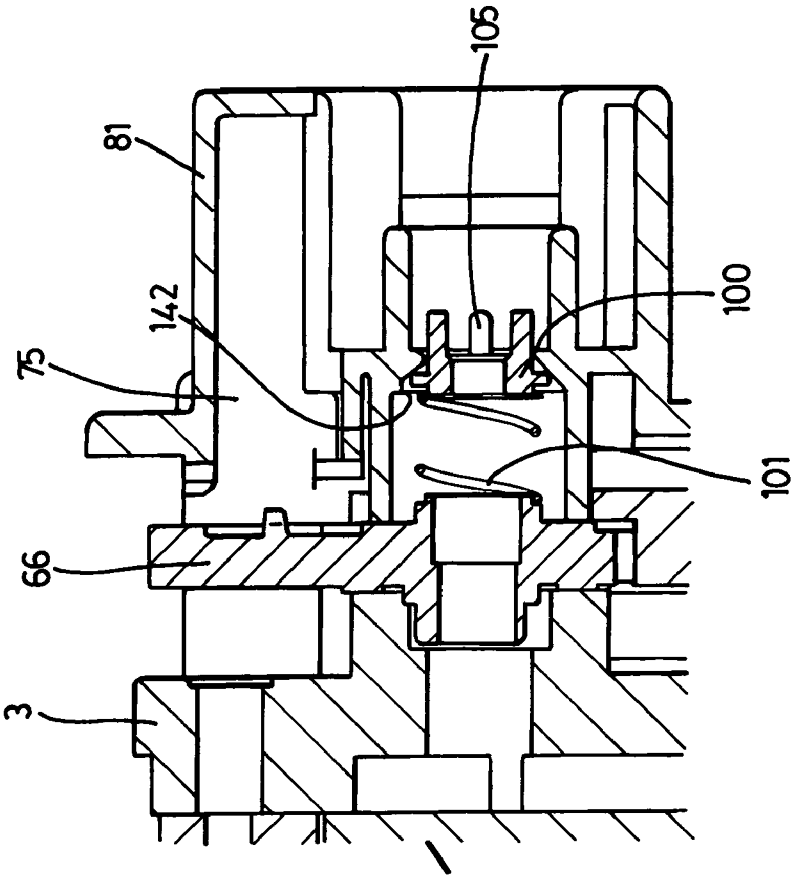
FIG. 23 is an enlarged view of a socket indicated by the enclosed region of FIG. 22.

FIGS. 22 and 23 show the components of FIGS. 1 and 2 in an assembled state. As is evident fasteners 84 are passed through aligned attachment holes 65, 36 of the intermediate plate 66 and the static valve member 3 respectively and into respective blind bores 120 of the housing 48. The transmission disc, the spring 44 and the rotatable valve member 2 are thus contained within the housing 48. The action of the spring 44 is to cause the rotatable valve member 2 to resiliently bear against the rearward face of the static valve member 3 and be in fluid sealing engagement therewith.

Figure 3:
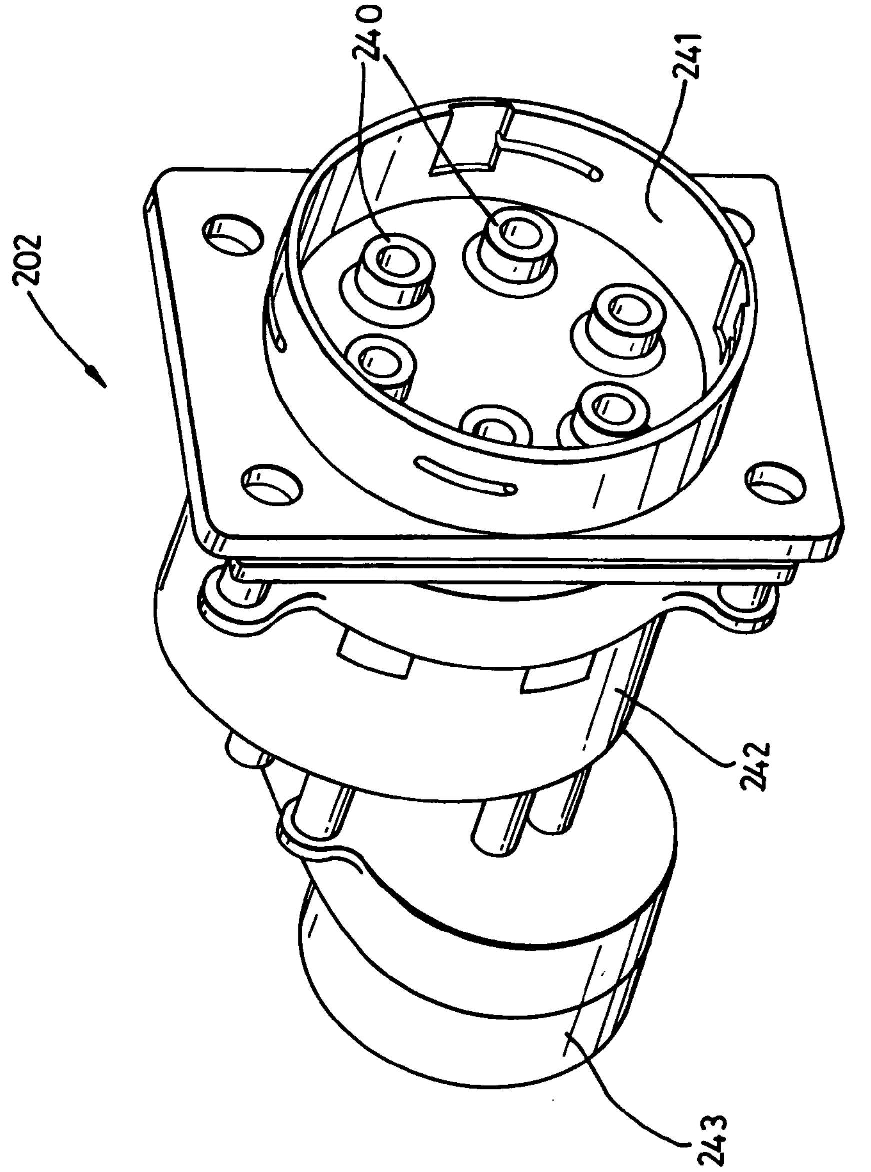
FIG. 3 is a perspective view of the of the socket/valve assemblies of the assembly of FIG. 1.

FIG. 3 shows the valve/socket arrangement 202 in an assembled state wherein the socket comprises an annular wall 241 and six ports 240, and said socket is configured to receive a suitably dimensional plug of a pressure garment/support. Each of the ports 241 is adapted to be connected to a respective conduit of a suitable plug with each conduit being connected to an inflatable cell or a group of inflatable cells.

Rearward of the socket there is provided a housing 242 which accommodates, inter alia, rotatable and static valve components very similar to those described above. Moving further rearward there is provided an optical disc and sensor device for sensing the angular position of the rotatable valve component. Lastly a housing 243 accommodates a motor for driving the rotatable valve component.

As best can be seen in FIG. 2 the pump assembly 200 further comprises a control PCB 160.

The control PCB 160 is provided with control data which is representative of instructions for various inflation/deflation sequences for the respective valve/socket assemblies 201 and 202. In particular the data relates to how the rotatable valve components and the pump unit are controlled so as to achieve a particular inflation/deflation sequence.

The PCB 160 is provided with an input signal from the keypad 203, and with inputs from the pressure and rotational position sensors of each valve/socket assembly.

The pneumatic pump unit 210 of known type is adapted to provide pressures between 20 and 120 mmHg. The unit comprises two electromagnetically oscillating reed assemblies, used to drive two pairs of diaphragms and non-return valves. Use of two oscillating reed assemblies enables the unit to be balanced and acoustically quiet.

Figure 24:
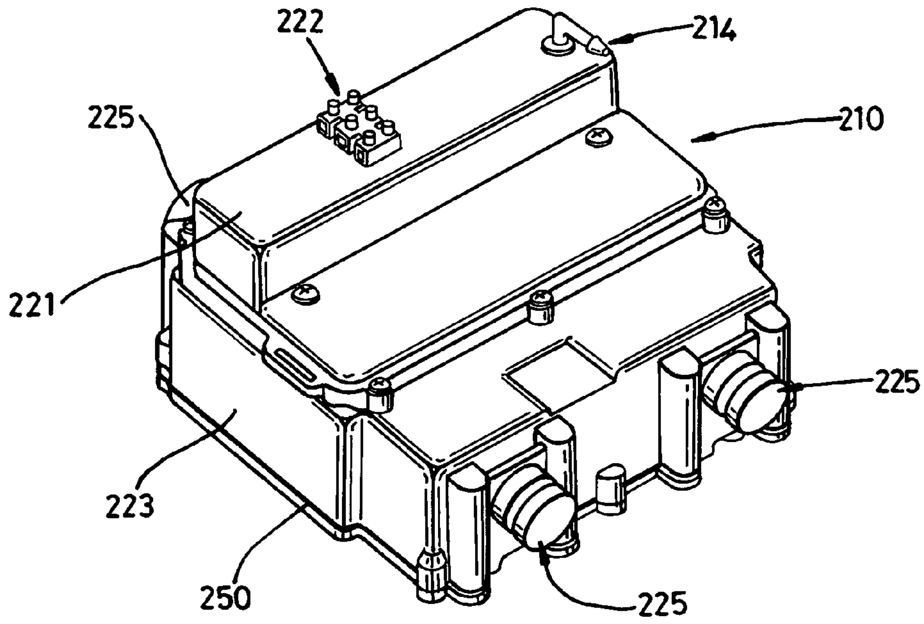
FIG. 24 is a perspective view of an inner housing of the pump assembly of FIG. 1.
Figure 25:
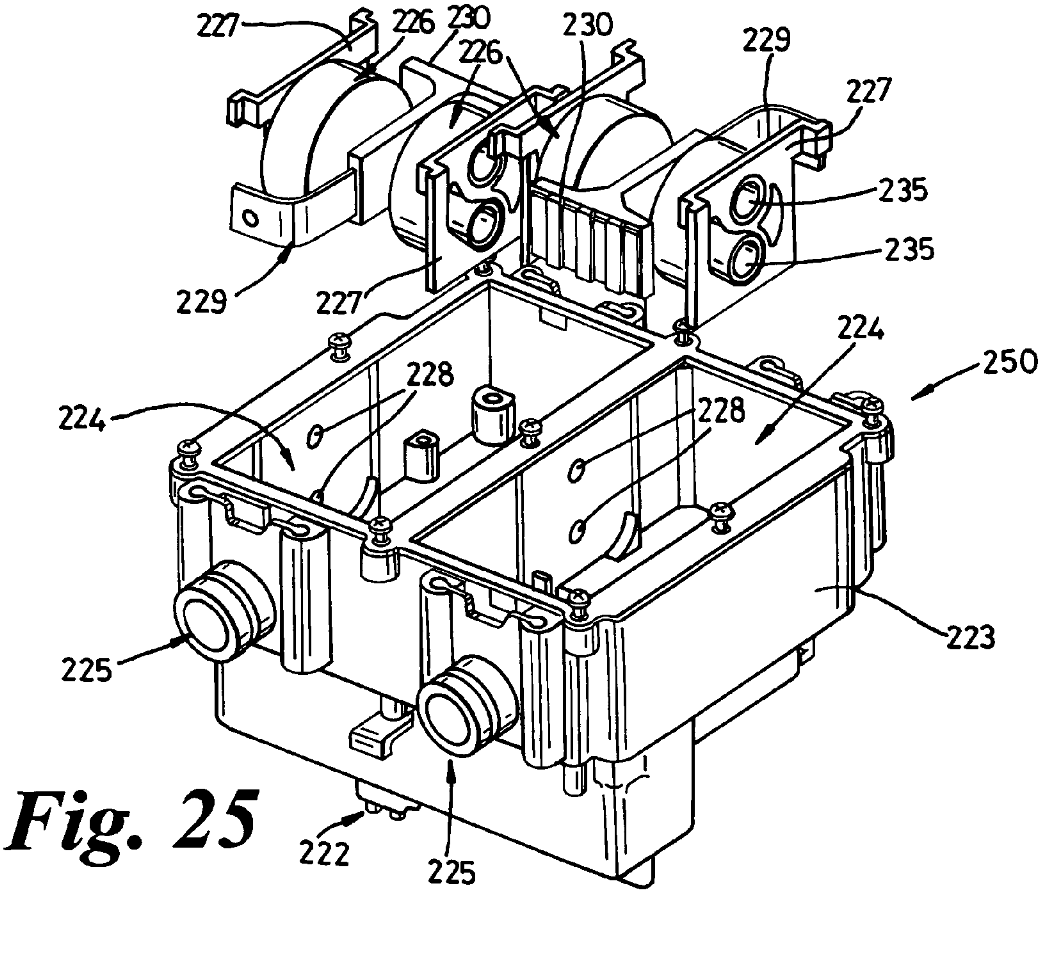
FIG. 25 is an exploded perspective view of the inner housing of FIG. 24.

FIGS. 24 and 25 show the innards of the pump assembly which comprises an internal housing 250 which is provided with four anti-vibration mounts 225 which contact with the external housing. An uppermost part 221 of the internal housing 250 comprises an electrical terminal box (unreferenced) to which the terminations are shown at 222. The housing part 221 further comprises a series of moulded baffles which form a silencer. The principal part 223 of the inner housing comprises two chambers 224 which are each adapted to receive an oscillating reed assembly. Each assembly comprises two diaphragms 226 that act as bellows. The diaphragms 226 are sandwiched between two mounting plates 227, each mounting plate 227 being provided with two non-return valves 235 which are fitted in opposing orientations so as to allow air in and out with each oscillation.

Each pair of diaphragms 226 are actuated by a respective reed oscillator which comprises a resilient end 229 and a free end 230 which is provided with a permanent magnet.

In use respective coil assemblies in parts of the housing adjacent the free ends 230 have alternating currents passed therethrough so causing the reed oscillators to oscillate in phase. Inlet and outlet apertures formed in the housing 223 and located in register with the non-return valves allow air to be drawn into each diaphragm and urged out respectively towards common air outlet elbow 214.

With reference to FIG. 4 the common air outlet 214 is connected to inlets 213 which direct air to respective valve/socket arrangements 201 and 202 via respective non-return valves 215. Each valve/socket assembly is provided with a pressure sensor 220 which is configured to measure the pressure of air in a cell or a group of cells of a garment or support.

By way of example the sockets 209' are adapted to receive plugs of pressure of therapy garments, for example a calf garment and a foot garment, and the socket 202 is adapted to receive the plug of a support, for example a mattress. Where three therapeutic inflatable cell apparatus are connected to the assembly 200 the control PCB is capable of simultaneously implementing respective inflation/deflation sequences for both valve/socket arrangements. It should be noted that the same inflation/deflation sequence is applied to both garments connected to the sockets 209, however the garments may consist of a calf garment and a foot garment.

The control PCB 160 is configured such that whenever either of the inflation/deflation sequences requires air to be fed into a garment/support the pump unit 210 is activated, otherwise the pump is not activated. In other words an 'on-demand' system is used. It is evident therefore that the pump unit 210 is of a sufficient capacity to be able to provide air to three inflatable cell apparatus simultaneously.

It will be appreciated that the control PCB may be programmed to be capable of implementing more than one inflation/deflation sequence for each valve/socket assembly, and there may also be the possibility of a user being able to vary an inflation/deflation sequence (within certain parameters).

The operation of the assembly 200 when connected to a pressure therapy garment is now described. A pressure therapy garment (for example a calf or a leg garment) is connected to one of the sockets 209'. The plug 130 is connected to the garment (not illustrated) by way of three flexible plastic tubes 132 (as seen in FIG. 22) which provide fluid communication with respective cells of the garment.

As is seen best in FIG. 22 inner conduits 131 of the plug 130 engage with the limbs 105 of the respective valve plates 100 and urge said valve plates in a rearward direction against a resilient force of the associated springs 101 thus providing fluid communication between the inflatable cells of the garment and the ports 14, 15, 16, 17, 18 and 19 of the static valve member 3.

With reference to FIG. 23 when the valve plates 100 act to seal the conduits 83 (ie when a therapy garment connector is not present or is not correctly positioned in a respective socket) said valve plate is seated on a chamfered shoulder 142.

As previously described the optical disc 41 enables the angular position of the rotatable valve member to be determined. The slot 52 is wider than the other slots 51 so as to indicate 0° position. As the optical disc is rotated the disc 41 will periodically block light from reaching the light detecting device provided on the limb 61 and will result in a signal that is effectively a square wave. Thus the slot 52 will produce a 'pulse' of longer duration which is indicative of 0° position and the number of subsequent pulses produced by the narrower slots 51 will determine the angular displacement from the 0° position. Since twenty four slots are provided the optical disc 41 enables a resolution of 15°. Signals from the sensor arrangement 42 are sent to the data processor of the PCB 160 and the rotatable valve member is rotated to a desired angular position in response to stored information as to a current angular position and the (feedback) signal received from the sensor arrangement 42 as the optical disc is rotated.

During a start-up procedure it is first determined whether zero, one or two therapy products are connected to the pump assembly. On start up, the PCB 160 issues a signal to index the optical disc 41 first to the 0° and then to the 75° position, the first inflation position for the first pressure therapy product. A pulse of air of approximately 0.2 seconds duration is issued and the resulting back pressure in the rotatable valve assembly is measured by a pressure sensor 220 and logged. If a back pressure below a predetermined stored value is detected, this indicates that a product plug 130 is present in the corresponding connector socket because the air pulse is delivered past the opened valve plates 100 and into effectively an infinite volume. If a back pressure above the predetermined pressure value is detected, this indicates that there is no product present, because the closed shut off valve 100 results in the air pulse being delivered into the relatively small enclosed volume in the rotatable valve assembly.

The PCB 160 then issues a signal to rotate the optical disc 41 to the 255° position, this is the first inflation position for the second product. The air pulse and detection procedure described above is repeated, and the PCB determines if a therapy product is present in the second connector socket of the valve/socket assembly 201. The process is then further repeated for the socket of the valve/socket assembly 202.

The PCB 160 can now determine whether zero, one or two therapy products are present. The user is then required to manually inform the PCB 160, by way of the user keypad 203, of the type or types of therapy garment which is/are connected. For example, one or two leg garments could be attached, one or two foot garments could be attached, or a combination of two different product types could be attached.

The required pressure control data stored in the memory of the PCB 160 for the particular therapy product type is then retrieved.

Figure 28:
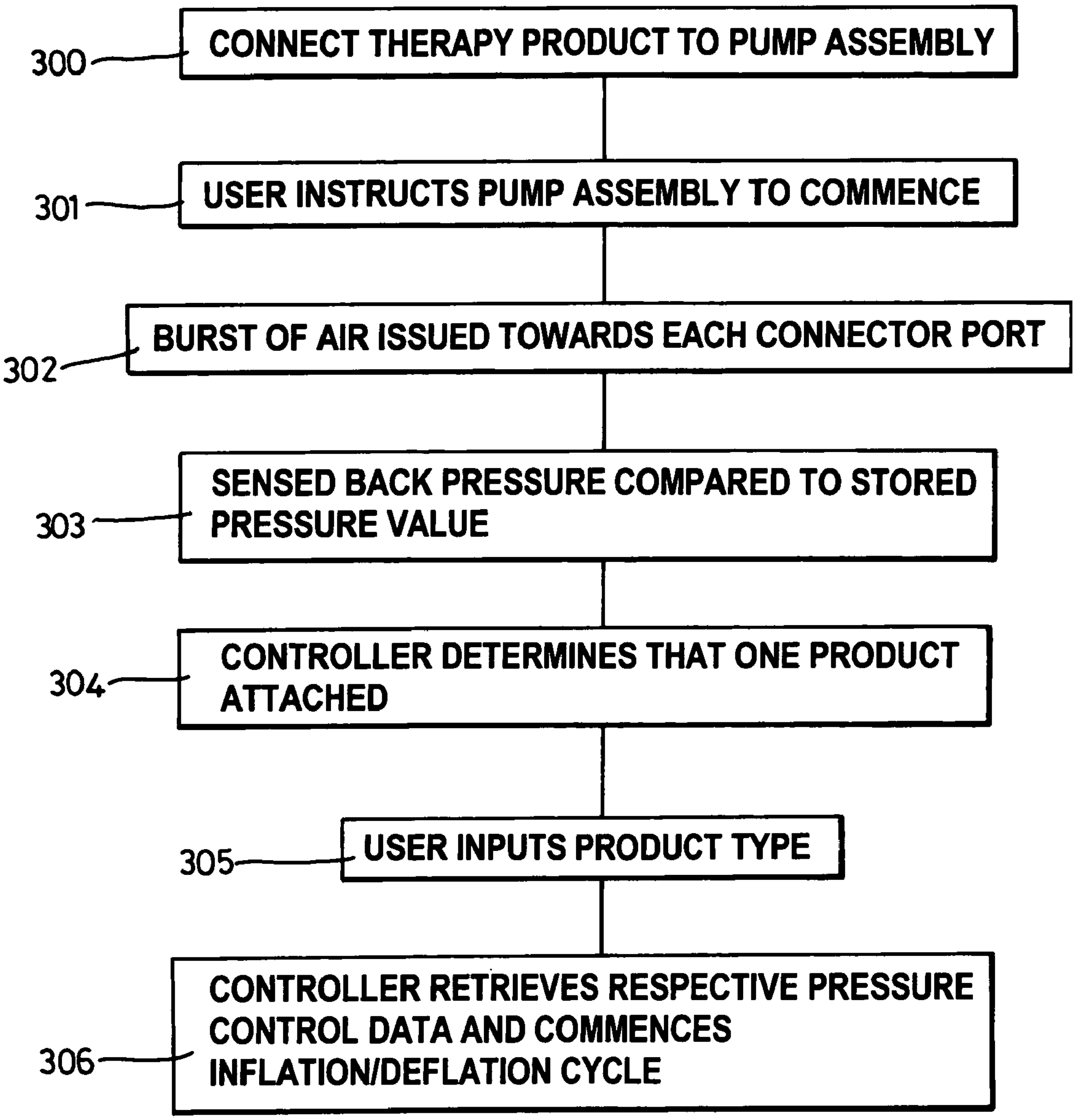
FIG. 28 is a flow diagram of process steps to determine connection status of a therapeutic inflatable cell apparatus.

FIG. 28 shows the various process steps 300 to 306 executed during the start-up procedure.

A pressurised air inlet 110 is connected to the pneumatic pump 210, such that in use air is urged into the housing 48.

Figure 17:
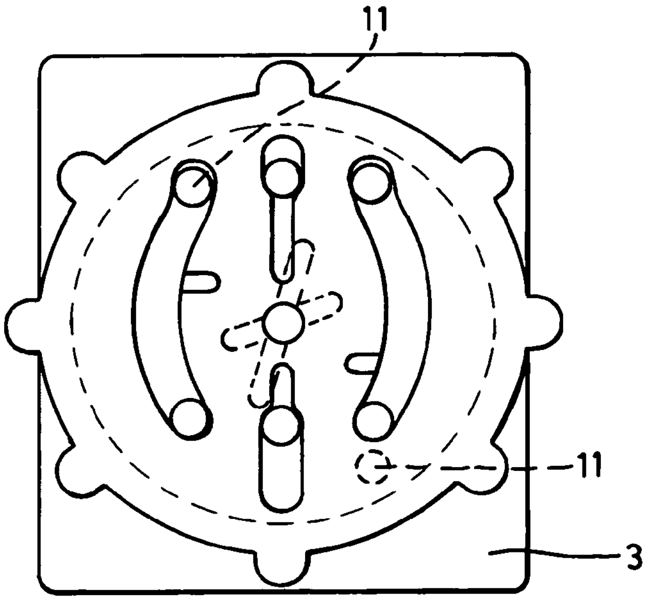
FIG. 17 is a rear elevation of the static valve member onto which the outline of the rotatable valve member in a first position has been superimposed

The rotatable valve member 2 is initially rotated to 75° from the 0° position as shown in FIG. 17. In this position air is able to pass through one of the ports 11 and into port 14 of static valve member 3 and into port 16 of the same by virtue of the channel 21. The pressure sensor 220 monitors the pressure of air in each of the conduits 83 which pressure measurements correspond to the pressure in the respective cells of the garment. It is important to note that the inflation time (i.e. the time for which the rotatable valve member 2 is held in a particular position) is dependent on the pressure measurements and not on a predetermined time. Signals indicative of the pressure readings are sent to the control PCB 160 from the pressure sensor 220 which is located in port 121 (see FIG. 2), in the housing 46.

Figure 18:
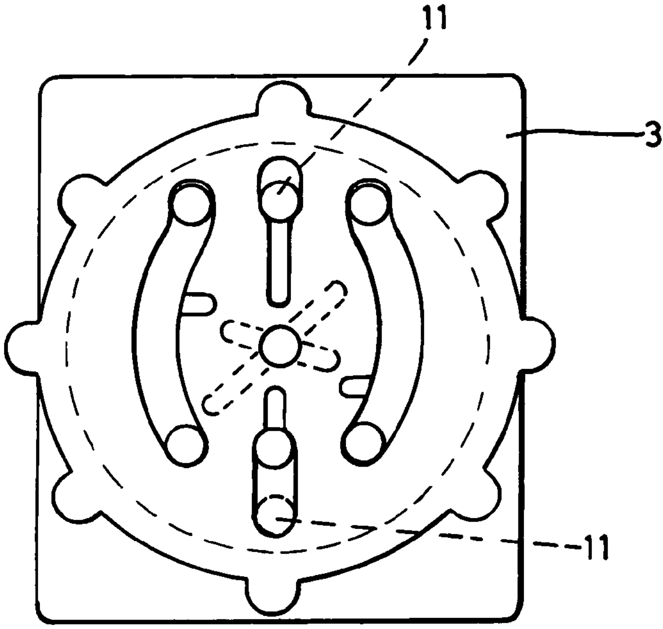
FIG. 18 is similar to FIG. 17 with the rotatable valve member shown in a second position.

Once the predetermined pressure is reached the rotatable valve member is rotated to the 105° position shown in FIG. 18 so that one of the ports 11 is brought into alignment with the upper channel 25 and the other port 11 is brought into alignment with the lower channel 28. In such a position air is caused to inflate the cells which are in communication with the parts 15 and 18.

Figure 19:
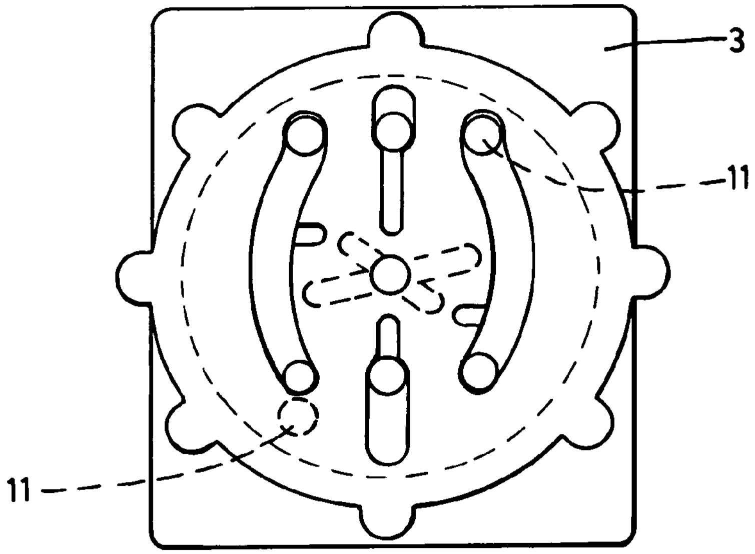
FIG. 19 is similar to FIGS. 17 and 18 with the rotatable valve member in a third position.
Figure 20:
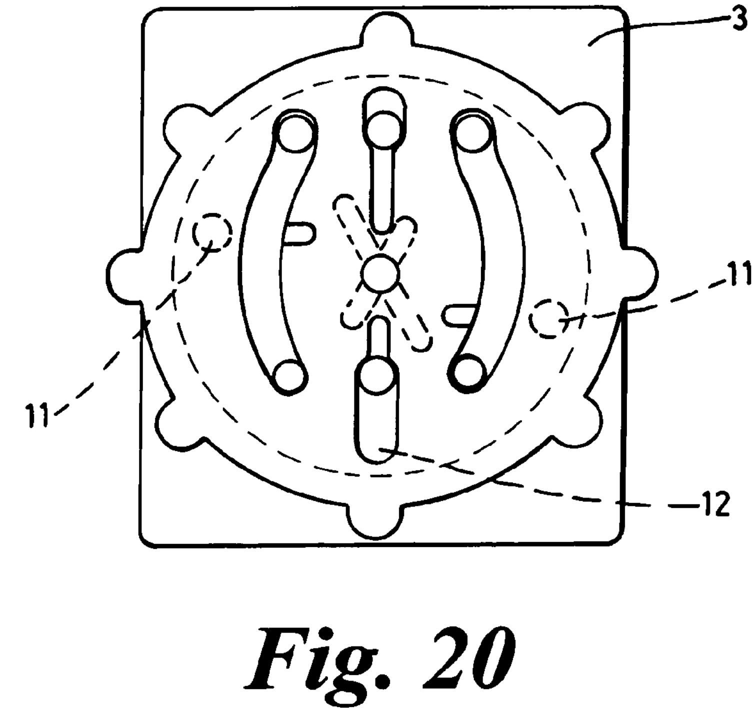
FIG. 20 is similar to FIGS. 17, 18 and 19 with the rotatable valve member shown in a fourth position.

FIG. 19 shows the rotatable valve member in the 135° position in which the cells in communication with ports 16 and 19 of the static valve member 3 are inflated. The port 19 receives a supply of air via the channel 22.

The rotatable valve member is then rotated into the 80° position in which the blind recess 10 is brought into fluid communication with the branch channel portions 23 and 24 and the lower channel 26 and the upper channel 27. In such a position the ports 14, 15, 16, 17, 18 and 19 are brought into fluid communication with the aperture 20 via the recess 10. The aperture 20 is open to atmosphere and thus all the cells of both garments are deflated. The deflation process is similarly controlled in response to pressure measurements as described above.

Figure 21:
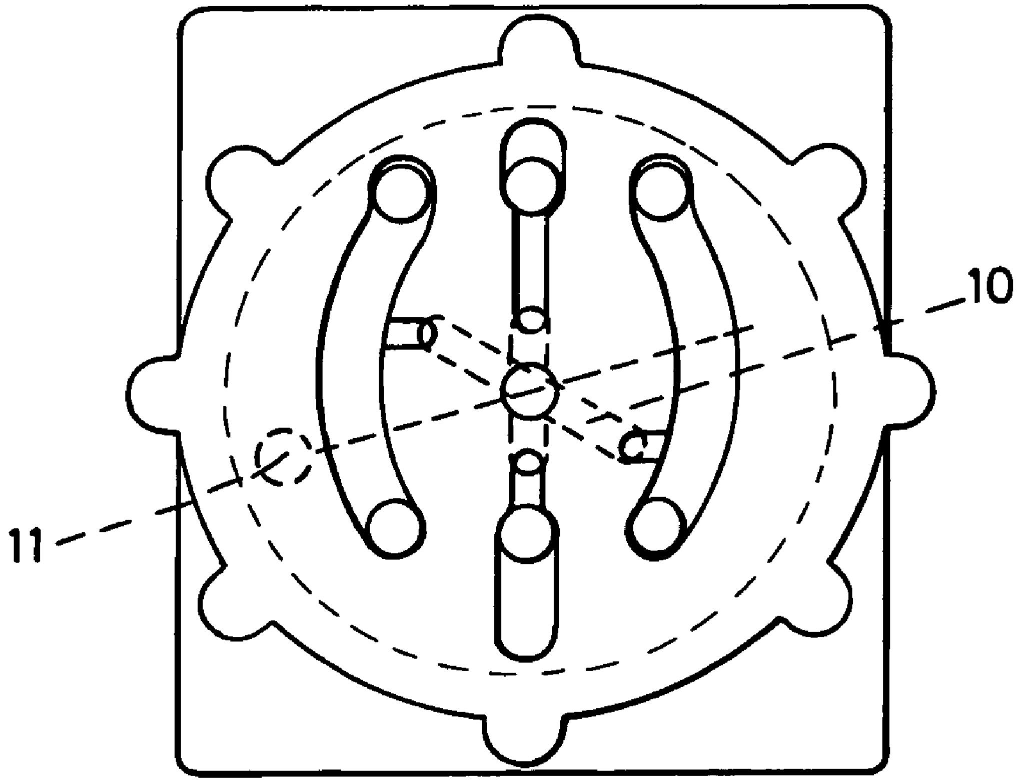
FIG. 21 is similar to FIGS. 17, 18, 19 and 20 with the rotatable valve member shown in a fifth position.

Two further positions of the rotatable valve member 2 are attainable, one of which is shown in FIG. 21. The port 12 is brought into alignment with the lower channel 28 so as to perform a so called kinked tube test on the centrally located connection tube between a plug in the lower socket 82 and the respective garment. If pressures above a predetermined level are measured in a selected conduit 83 then the PCB 160 causes an alarm signal to be activated.

A further kinked tube test is also effected for the connection tube in communication with the port 15.

As should now be evident one rotation through 360° of the rotatable valve member 2 results in two inflation/deflation cycles.

A significant advantage of the above described pump assembly 200 is that up to two different inflation/deflation sequences can be performed on up to three different therapeutic inflatable cell apparatus simultaneously from a single pump unit. In a modified embodiment additional sockets and/or socket/valve assemblies are provided so that additional inflation/deflation sequences can be performed simultaneously on additional therapeutic inflatable cell apparatus.

It will be appreciated that the control PCB may be programmable to alter one or more parameters of stored inflation/deflation sequences.

While this invention has been described in conjunction with the specific embodiments described above, it is evident that many alternatives, combinations, modifications and variations are apparent to those skilled in the art. Accordingly, the preferred embodiments of this invention, as set forth above are intended to be illustrative only, and not in a limiting sense. Various changes can be made without departing from the spirit and scope of this invention.

The invention claimed is:

1. A therapeutic inflatable cell apparatus pump assembly, the assembly comprising a common pump unit, a controller, and first and second valves, each of the valves comprising a cycle control valve member, said cycle control valve member being provided with at least one fluid passageway and each of the valves being adapted to be positioned to predetermined positions so as to regulate fluid quantity in respective therapeutic inflatable cell apparatus, wherein the first valve being adapted to perform at least one respective therapeutic inflation/deflation sequence for its respective therapeutic inflatable cell apparatus which is different from at least one therapeutic inflation/deflation sequence which the second valve is arranged to perform, wherein the controller is provided with control data, the control data being representative of instructions for controlling the pump unit and the valves to perform the respective therapeutic inflation/deflation sequences, and the assembly further comprising a first socket associated with the first valve and a second socket associated with the second valve for connection to its respective therapeutic inflatable cell apparatus to supply air from the respective valve, the assembly being such that when air is required to be supplied to at least one of the valves for a therapeutic inflation/deflation sequence, the controller activates the common pump unit and air is pumped to an air outlet of the pump to feed air to the valves, wherein the first and second valves are operable both singularly and simultaneously to singularly or simultaneously supply air to the first and second sockets.

2. A pump as claimed in claim 1 which is adapted to allow multiple inflatable cell apparatus to operate simultaneously and at least two of the inflatable cell apparatus being subjected to different therapeutic inflation/deflation sequences.

3. A pump assembly as claimed in claim 1 which is adapted to effect a therapeutic inflation/deflation sequence comprising at least one or a combination of (i) inflating at least one cell of an inflatable cell apparatus to a particular pressure, (ii) maintaining a predetermined pressure in at least one cell of an inflatable cell apparatus for a predetermined time, (iii) inflating and /or deflating cells in a particular sequence, (iv) inflating and/or deflating at least one cell at a particular rate of inflation and/or deflation.

4. A pump assembly as claimed in claim 1 in which the common pump unit consists of one pneumatic pump unit.

5. A pump assembly as claimed in claim 1 in which the cycle control valve member comprises a rotatable valve member which is adapted to be rotated to predetermined angular positions.

6. A pump assembly as claimed in claim 5 in which each of the valves further comprises a static valve member, said static valve member being provided with at least one fluid passageway which is adapted to be communicable with the inflatable cell apparatus and the rotatable valve member being arranged to be rotatable with respect to the static valve member.

7. A pump assembly as claimed in claim 1 in which the predetermined positions are indexed so that cells of the therapeutic cell apparatus can be selectively inflated.

8. A pump assembly as claimed in claim 6 in which the rotatable valve member is provided with at least one fluid passageway for inflation of at least part of the inflatable cell apparatus and with at least one fluid passageway for deflation of at least part of the inflatable cell apparatus, and in use the rotatable valve member can be rotated to predetermined angular positions to effect at least one of inflation and deflation of the apparatus.

9. A pump assembly as claimed in claim 8 in which the rotatable valve member is rotatable with respect to the static valve member so as to determine whether a fluid passageway of the static valve member is brought into fluid communication with one of an inflation passageway and a deflation passageway of the rotatable valve member.

10. A pump assembly as claimed in claim 6 in which the static valve member is provided with at least two sets of a plurality of fluid passageways, each set of passageways being adapted to be associated with a respective inflatable cell apparatus.

11. A pump assembly as claimed in claim 1 in which the controller is connected to a position sensor for sensing the condition of the valves and to a pressure sensor for measuring pressure in at least one cell of an inflatable cell apparatus.

12. A pump assembly as claimed in claim 11 in which the controller is configured to control the pump unit and the valves in response received signals from the position sensor and the pressure sensor, compare said pressure and position signals to the control data and operate at least one of the valves and the pump unit as required.

13. A pump assembly as claimed in claim 12 in which the controller comprises a rotatable component which is connected to the cycle control valve member and is provided with a plurality of angularly spaced index features, and the controller further comprising a position sensor device, and in use, rotation of the rotatable component causes the index features to selectively control light received by the position sensor device.

14. A pump assembly as claimed in claim 1 in which at least one of the sockets is adapted to receive a plug of the therapeutic inflatable cell apparatus.

* * * * *